(12) United States Patent
De Maria

(10) Patent No.: US 8,580,236 B2
(45) Date of Patent: Nov. 12, 2013

(54) HAIR SUSTAINING FORMULATION

(76) Inventor: Richard P. De Maria, Highland Mills, NY (US)

( * ) Notice: Subject to any disclaimer, the term of this patent is extended or adjusted under 35 U.S.C. 154(b) by 1123 days.

(21) Appl. No.: 12/074,898

(22) Filed: Mar. 7, 2008

(65) Prior Publication Data

US 2008/0233213 A1    Sep. 25, 2008

Related U.S. Application Data

(60) Provisional application No. 60/895,706, filed on Mar. 19, 2007.

(51) Int. Cl.
| | | |
|---|---|---|
| *A61K 127/00* | (2006.01) | |
| *A61K 131/00* | (2006.01) | |
| *A61K 135/00* | (2006.01) | |
| *A61K 33/00* | (2006.01) | |

(52) U.S. Cl.
USPC ............................ 424/70.1; 424/725; 426/600

(58) Field of Classification Search
None
See application file for complete search history.

(56) References Cited

U.S. PATENT DOCUMENTS

| | | | |
|---|---|---|---|
| 5,750,107 A | 5/1998 | Nomura | |
| 5,750,108 A | 5/1998 | Edwards | |
| 6,333,057 B1 | 12/2001 | Crandall | |
| 6,338,855 B1 * | 1/2002 | Albacarys et al. | 424/409 |
| 6,358,541 B1 | 3/2002 | Goodman | |
| 6,376,557 B1 | 4/2002 | Zaveri | |
| 6,596,266 B2 | 7/2003 | Catalfo et al. | |
| 6,733,776 B1 | 5/2004 | Li et al. | |
| 7,094,569 B2 | 8/2006 | Kim et al. | |
| 7,166,300 B1 | 1/2007 | Dascalu | |
| 7,166,366 B2 | 1/2007 | Moser | |
| 7,175,842 B2 | 2/2007 | Morgan et al. | |
| 7,211,274 B2 | 5/2007 | Ho et al. | |
| 7,223,562 B2 | 5/2007 | Sun et al. | |
| 2004/0067890 A1 * | 4/2004 | Gupta | 514/18 |
| 2004/0082495 A1 * | 4/2004 | Maleeny et al. | 512/1 |
| 2004/0171693 A1 * | 9/2004 | Gan et al. | 514/565 |
| 2005/0209131 A1 | 9/2005 | Singleton | |
| 2006/0216258 A1 * | 9/2006 | Singleton et al. | 424/70.12 |

OTHER PUBLICATIONS

Jun. 2005 http://www.ishrs.org/nonsurgical/options-rogaine.htm.*
2010 http://www.globalherbalsupplies.com/herb_information/saw_palmetto.htm.*
Hrs et al., Therapy of alopecia, 2005, Farmaceutski Glasnik, 61: 621-628.*
2010 http://swiftcraftymonkey.blogspot.com/2010/02/msm-aka-dimethyl-sulfone.html.*
Dr. R. N., "Looking Into Emu Oil", University of Massachusetts, Oct. 2001 published on-line: http://www.pure-emu-oil.com/emu-oil-research.html.
Kimberly Pryor, "Patented Formula Designed to Alleviate Pattern Hair Lossw in Men and Women": published on-line.http://www.vrp.com/articles.aspx?ProdID=art823&zTYPE=2, 2013.
D. H. Rushton, et. al., "Causes of Hair Loss and the Developments in Hair Rejuvenation," published on-line: http://www.blackwell-synergy.com/doi/abs/10.1046/j.0412-5463.2001.0, 2001.

* cited by examiner

*Primary Examiner* — Patricia Leith
*Assistant Examiner* — Catheryne Chen
(74) *Attorney, Agent, or Firm* — Oktay Enterprises Int'l., LLC; Sevgin Oktay

(57) ABSTRACT

A multi-dimensional hair sustaining formulation having a liquid transport agent that carries multi-ingredients to hair follicles in order to prevent Dihydrotestosterone (DHT) from attaching to receptor sites on the follicles of existing hair, hence promoting the protection and continued growth of existing hair—which otherwise would succumb to DHT attack and loss—rather than trying to re-grow hair that has already been lost.

11 Claims, 1 Drawing Sheet

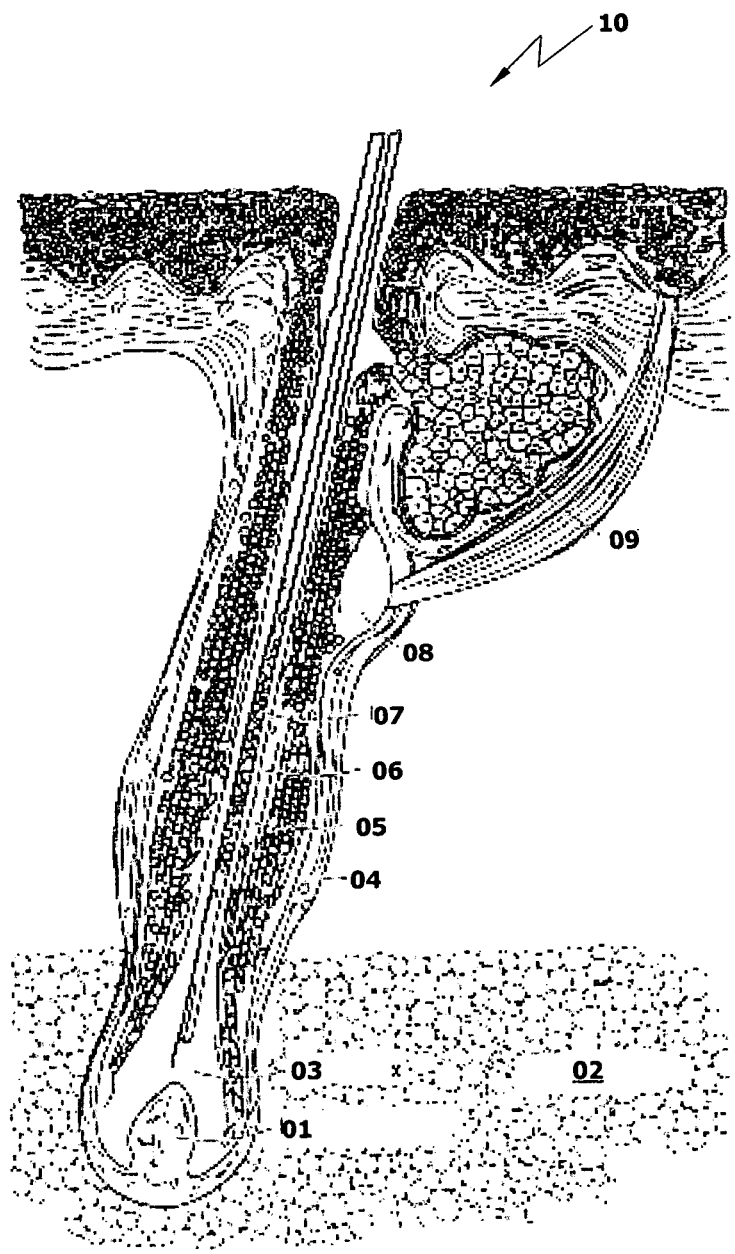
Prior Art

HAIR SUSTAINING FORMULATION

This application claims priority under 35 U.S.C. ¶119 (e) of U.S. Provisional Patent Application Ser. No. 60/895,706 filed 19 Mar. 2007, the contents of which are incorporated herein by reference.

BACKGROUND

All references cited in this specification, and their references, are incorporated by reference herein where appropriate for teachings of additional or alternative details, features, and/or technical background.

Disclosed is a formulation which promotes and sustains the rejuvenation and continued growth of existing hair. Though prior art is abound with many different formulations that promote the re-growth of lost hair on the same scalp, that approach has been found to be a difficult task at best. It is desirable to control the problem of hair loss when it is first detected and prevent further loss by a judicious application of an effective formulation rather than trying to re-grow the hair that has already been lost.

Biological sciences have determined that humans typically have about 100,000 to 150,000 hairs on their scalps. The life of each hair is subject to a cycle, known as the pilar cycle. During the pilar cycle, hair forms, grows and falls out, before being replaced by a new hair shaft, which appears in the same follicle. As a reference, FIG. 1 shows a diagrammatic representation of a human hair 10 having a follicular papilla 01 embedded in a follicular bulb 02 in the scalp of a human being (not shown). Main elements of hair 10 comprise matrix 03, which also resides in follicular bulb 02, adventitial sheath 04, outer root sheath 05, inner root sheath 05, hair shaft 07, "der Wuist" or the "bulge" 08, the sebaceous gland 09. The features of human hair are well known in the art and, therefore, they are not described in detail here in order not to unnecessarily obscure the present invention.

It is described in U.S. Pat. No. 5,750,108, that the pilar (related to hair) cycle can be broken down into three successive phases: the anagen phase, the catagen phase and the telogen phase. During the anagen phase, the hair undergoes a period of active growth associated with an intensive metabolic activity in the bulb. The subsequent catagen phase is transitory and marked by a slowing-down of the mitotic activity. The final telogen phase corresponds to a period of rest for the follicle, with the hair being shed.

It is further known that androgenetic alopecia (baldness) is a disorder that afflicts millions of men and women. Alopecia occurs when the pilar cycle becomes accelerated or disturbed. In other words, alopecia occurs when the growth phases are shortened, and the hairs proceed to the telogen phase earlier, shedding in large numbers. The successive growth cycles lead to increasingly thinner and increasingly shorter hairs, converting gradually to an unpigmented down.

Hair follicles are known to be sensitive to androgens. In particular, the pilar cycle of some hair follicles, such as those on scalp, respond to androgens in the manner noted above, i.e., by displaying shortened anagen (growth) phases of the hair cycle, by displaying an increase in the amount of finer-textured, shorter hairs, and by displaying an overall reduction in the diameter of hair follicles.

Testosterone is the principal circulating androgen in humans. Testosterone is secreted by the testes, ovaries, and adrenal glands. Testosterone can act on body tissues directly or it can serve as a prehormone for tissues that utilize its major active metabolic products-estradiol and dihydrotestosterone (the later also being referred to as "DHT").

Although the testes make dihydrotestosterone, most of the dihydrotestosterone circulating in blood comes from peripheral tissue conversion of testosterone. Dihydrotestosterone is formed from testosterone in a reaction catalyzed by the enzyme 5-alpha reductase, which is found in a large number of tissues.

An important aspect of the androgen action is the binding of testosterone or dihydrotestosterone to the androgen receptor. The androgen receptor has been located in specific skin structures, including the hair follicle and sebaceous gland. Dihydrotestosterone (DHT) has been shown to bind to the androgen receptor with higher affinity than testosterone and is the major androgen implicated in the changes in the pilar cycle, resulting in the balding scalp.

As further described in described in U.S. Pat. No. 5,750,108, there are various types of antiandrogens, and they vary in their mode of action. Some antiandrogens block enzyme reactions and limit the formation of potent androgens. Other antiandrogens work by specifically blocking the androgen receptor, and still other agents have an effect on both the enzyme and the receptor. Thus, in treating the balding scalp, effective antiandrogens include those that either block the metabolism of testosterone by inhibiting 5-alpha reductase, or inhibit Dihydrotestosterone (DHT) binding to the androgen receptor, or both.

Conventionally, antiandrogens have been used for quite some time to retard hair loss or stimulate hair growth for patients. Some treatments are orally administered, which has the undesirable effect that the entire body is exposed to the treatment compositions. Other treatments are applied topically (over the skin). However, these treatments are less effective than they might otherwise be, because the entrance to the hair follicles is obstructed.

Specifically, the applicant has experimented with antiandrogens, including products called Follicare™ and DHT Blocker™. The applicant first tried Follicare™ in pill form for about a year, but to no avail. Then he switched to DHT Blocker™, also in pill form for another year with still no results. The applicant also used Saw Palmetto to treat potential prostate problems, which is also claimed to promote hair growth. After many years of useage, there was still hair loss. He reasoned that these products may not be effective due to mal-absorption issues in the digestive tract. He then experimented with different ingredients and a transport agent to deliver the ingredients to the hair follicles. Working with a chemist, the applicant designed a formulation in a liquid form in which at first some of the unexpected ingredients such as copper peptide and Emu Oil, which did not emulsify in the transport agent. However, with continued and persistent experimentation, the applicant has been able to derive formulations, which stop Dihydrotestosterone (DHT) from attacking hair follicles, and help sustain the growth of existing hair.

REFERENCES

U.S. Pat. No. 7,223,562 discloses compositions for controlling hair growth. FP-1 is a protein that is specifically expressed in the follicular papilla of the hair follicle. The nucleic acid and amino acid sequences of FP-1, as well as antibodies that specifically bind FP-1 are provided. In addition, methods of isolating follicular papilla cells and methods of modulating hair growth are also disclosed.

U.S. Pat. No. 7,094,569 describes hair follicle growth factor proteins. The invention relates to hair follicle growth factor (HFGF) proteins, genes encoding HFGFs, methods for preparing HFGF proteins and therapeutic uses of HFGF proteins. The HFGF proteins of the invention have a characteristic reduced expression in hair follicles derived from alopecia patients and have a stimulatory effect on hair follicle cell proliferation. HFGF proteins may be used to prevent or treat alopecia and to promote or accelerate hair growth and hair follicle repair U.S. Pat. No. 7,175,842 teaches methods of modulating hair growth. The invention features methods of promoting hair growth in a subject. The methods include inducing or mimicking the effects of Wnt promoted signal transduction, e.g., by increasing the level of Wnt protein or administering an agent which mimics an effect of Wnt promoted signal transduction, e.g., by administering lithium chloride. Methods of inhibiting hair growth are also provided.

U.S. Pat. No. 7,211,274 shows hair growth formulation. The invention relates to a formulation for promoting hair growth and preventing hair loss. Supplementation with the formulation promotes hair growth and increases the number of hairs in mammals. In one embodiment, a composition for promoting hair growth and reducing hair loss according to the present invention comprises mixed tocotrienols and a pharmaceutically acceptable excipient.

U.S. Pat. No. 7,166,366 describes an agent for inducing hair growth containing extracts of Saw Palmetto and Swertia. The invention consists in a composition comprising a mixture of extracts of saw palmetto and swertia, of derivatives thereof and of active components being part of said extracts. The composition may comprise additional agents and/or extracts, for example, irritating agents, extracts for hair invigoration, hair nourishment agents, antidandruff antiproliferative compounds, extracts with an antimicrobial, extracts with an antifungal, extracts with anti-inflammatory agents, extracts with a steroid, extracts with a nitric oxide donor and extracts with minoxidil. The concentration of the saw palmetto extract in the composition is 0.01-100%. The composition may comprise a suitable carrier, solvent and/or emulgent. The composition may be, for example, an internally ingested tablet, a capsule, drops or a suspension. The invention relates also to the use of said composition in the preparation of a mixture for the application to humans and animals against the loss of hair and to method for the treatment with said composition for the treatment of humans and animals against loss of hair.

U.S. Pat. No. 6,733,776 teaches a method to provide hair growth by stimulating extrusion of hair from a hair follicle which employs a liposomal formulation of an active ingredient which stimulates extrusion when taken up by the hair follicles.

U.S. Pat. No. 6,358,541 shows topical preparation for the treatment of hair loss. Improved preparations for the treatment of androgenetic alopecia comprise saw palmetto berry extract containing phytosterols and one or more low irritability constituents that enhance penetration of the extract into hair follicular pores. The low irritability penetration enhancer(s) may be selected from the group consisting of adapalene, tretinoin, retinaldehyde, tazarotene, salicylic acid, azelaic acid, and glycolic acid. Also provided is a method for reducing hair loss by application to the scalp of the improved preparations.

U.S. Pat. No. 6,333,057 teaches composition and method for topical treatment of androgenic alopecia. The invention relates to the topical and oral treatment of hair loss, especially androgenic alopecia, by providing formulations that include anti-androgens, especially extracts of the saw palmetto plant, co-enzyme Q, and acetyl carnitine, and optionally stimulators of adenylate cyclase to stimulate hair growth, to increase the luster of hair, and to decrease hair graying.

U.S. Pat. No. 5,750,108 describes hair treatment system and kit for invigorating hair growth. A method for hair treatment is disclosed wherein a first treatment solution comprising tea tree oil is periodically applied to the scalp for at least 10 days. Then, a second treatment solution comprising chlorine dioxide is periodically applied to the scalp, immediately followed by application of an acidic solution having an acidity effective to release the oxygen in the chlorine dioxide solution, for at least 1 month. Finally, a third treatment solution comprising saw palmetto berry extract is periodically applied to the scalp for at least 1 month. Also disclosed is a hair treatment kit comprising a first treatment solution comprising tea tree oil, a second treatment solution comprising chlorine dioxide, an acidic solution having a pH effective to release the oxygen from said chlorine dioxide in said second treatment solution, and a third treatment solution comprising saw palmetto berry extract.

U.S. Pat. No. 5,750,107 discloses a hair growth promoter. The invention relates to a composition useful in as a hair growth promoter which contains an extract drawn from a plant having a pseudo bulb selected from the group consisting of Calanthe R. Br. and Phaius Lour. The extract can be obtained from either a portion of a plant or the pseudo bulb of Calanthe discolor Lindl, or Phaius flavus (Blume) Lindl by extraction of such a plant in an extraction solvent. The composition may include vitamins, amino acids, animal and plant oils, and sodium chloride. When applied to an area of skin afflicted with alopecia, the composition is useful for promoting hair growth.

SUMMARY

Aspects disclosed herein include a hair sustaining formulation having a liquid transport agent that carries multi-ingredients to hair follicles in order to prevent Dihydrotestosterone (DHT) from attaching to receptor sites on the follicles of existing hair; the liquid transport agent further comprising Emu Oil compound in a range from about 3.5 to 5.0% by weight; the multi-ingredients further comprising water from about 83 to 85% by weight, and Lysine HCl, Arginine, Dimethyl Sulfone, Steareth-20, Steareth-2, Camellia Sinensis, Ginkgo Biloba Extract, Vitis Vinifera, Biotin, Silica, Copper Tripeptide-1, Fragrance, PHENAGON® PDI (a cosmetic preservative comprising Phenoxyethanol and DMDM Hydantoin and Iodopropynyl Butylcarbamate); and antiandrogen ingredients comprising Serenoa Serrulata (aka Saw Palmetto), Copper Peptide, Methylsulfonylmethane (MSM; wherein the hair sustaining formulation promotes the protection and growth of the existing hair which otherwise would succumb to DHT attack and loss.

a method comprising the steps of preparing one or more Phases or batches of antiandrogen ingredients selected from the group consisting of Lysine HCl, Arginine, Dimethyl Sulfone, Steareth-20, Steareth-2, Serenoa Serrulata, Camellia Sinensis, Ginkgo Biloba Extract, Vitis Vinifera, Biotin, Silica, Copper Tripeptide-1, Fragrance, Phenagon; forming a first Phase A batch comprising ingredients water, Lysine HCl, Arginine, Dimethyl Sulfone; forming a second Phase B batch comprising ingredients liquid transport agent Emu Oil, Steareth-20, Steareth-2; forming a third Phase C batch comprising ingredients Serenoa Serrulata, Camellia Sinensis, Ginkgo Biloba Extract, Vitis Vinifera, Biotin, Silica, Copper Tripeptide-1, Fragrance, Phenagen PHENAGON®; and mixing the phases of the ingredients to form the topical hair sustaining solution.

BRIEF DESCRIPTION OF DRAWINGS

FIG. 1 shows a diagrammatic representation of a human hair shaft having a follicular papilla embedded in a follicular bulb in the scalp of a human being.

DETAILED DESCRIPTION

In embodiments there is illustrated:

a multi-dimensional hair sustaining formulation having a liquid transport agent that carries multi-ingredients to hair follicles in order to prevent Dihydrotestosterone (DHT) from attaching to receptor sites on the follicles of existing hair, hence promoting once again the growth of existing hair which otherwise would succumb to DHT attack.

In one embodiment, the present disclosure includes a Formula I comprising a composition for topical treatment of androgenetic alopecia having antiandrogen ingredients, including Emu Oil, Saw Palmetto and Copper Peptide, which are described further below.

In another embodiment, the present disclosure includes a Formula II comprising a composition of Formula I appended with ingredients Gingko Biloba, Silica and Methylsulfonylmethane/Dimethyl Sulfone (MSM) described below.

In yet another embodiment, the present disclosure includes a Formula III comprising a composition of Formula II further appended with ingredients Biotin and Green Tea Extract described below.

In still another embodiment, the present disclosure includes a Formula IV comprising a composition of Formula III further appended with ingredients L-Lysine, Grapeseed Extract and L-Arginine described below.

In one aspect of the disclosed Formulae I, II, III and IV, it will be noted that Emu Oil has been selected as the principal delivery agent of antiandrogens generally not found amongst the conventional delivery vehicles which optionally contain lechiin, isopropyl palmiatet, lecithin organogel, Pluronic F-127 organogel, NDMS, ethoxydiglycol:ethanol and/or water. In this aspect, the Emu Oil delivers the cited antiandrogen ingredients of Formulae I, II, III and IV to the hair follicle 01 shown in FIG. 1. It has been found that Emu Oil penetrates the epidermis layer of the skin (not shown) without body defenses rejecting it. This is explained by the fact that Emu Oil has a pH between about 5.0 to 7.0, which is close to the range of the pH of a healthy human body from about 6.1 to 7.0. pH is a measure of the acidity or alkalinity of a solution with a range of 1 indicating high acidity, 7 neutrality, and above 7, alkalinity.

In another aspect of the disclosed Formulae I, II, III and IV of the present disclosure, Emu Oil, unlike most oils, is 100% noncomedogenic, which is known not to clog pores of the skin. In comparison with other oils, Emu Oil has better moisturizing properties, superior texture and lower incidence of comedogenicity. Also it's not irritating to the skin. Studies also have shown that Emu Oil has a high concentration of non polar mono unsaturated fatty acids which promotes Emu Oil's ability to penetrate easily through the stratum corneum barrier (not shown). It is generally accepted that the stratum corneum is the least permeable layer of the epidermis. Some studies have also shown that Emu Oil alone promotes hair growth (See for example, http://www.pure-emu-oil.com/emu-oil-research.html.)

Of the antiandrogen ingredients disclosed above, Saw Palmetto in formula I is derived from the berry of the Saw Palmetto tree. This natural ingredient is comprised of fat soluble properties such as steroidal saponins, fatty acids, phytosterols, volatile oil, resins and tannins. Studies have shown a 32% reduction in DHT levels with the use of Saw Palmetto (See, for example http://www.vrp.com/articles.aspx?ProdID=art823&zTYPE=2. Furthermore, Formula I, with the presence of Saw Palmetto, indicated the blocking of Dihydrotestosterone (DHT) from attaching to receptor sites on the hair follicle 01 shown in FIG. 1.

The other ingredient in Formula I is Copper Peptide, which is used here to improve scalp condition by remodeling at the cellular level. Studies have shown that copper is key to the strength and flexibility of the skin. Recently, Copper Peptides have demonstrated its importance in tissue repair. It is found to actually accelerate tissue repair. Thus any damage to the tissue on the scalp is also repaired, creating a healthy environment for hair growth, and an increase in the size of the hair follicle.

In Formula II, Biloba Ginkgo provides the well-known antioxidants that help the aging process. Recently, it has been demonstrated that certain compounds in Gingko Biloba effectively dilate arties, veins and capillaries, which result in increased peripheral blood flow. It is this enhanced circulation of the blood that delivers nutrients throughout the body and in particular to the brain. By applying Gingko topically it is shown to aid in the circulation of blood flow and the delivery of nutrients to the hair follicle. Researchers in Japan have also observed that mice given Gingko had stimulated hair growth.

Silica in the same Formula II is normally found in high levels in skin and hair but these levels decrease significantly as aging progresses. By adding Silica to this formulation, it replenishes minerals to aid the body processes needed for structural health. It is also required for the proper functioning of the enzyme prolyhydroxylase. This enzyme aids in the formation of collagen, cartilage, connective tissue and blood vessels. Coupled with Methylsulfonylmethane (MSM), Formula II increases blood flow which aids in the delivery of nutrients essential to the hair. Sulfur compound aids in this process. MSM is responsible for making collagen and keeping the flexible bond between cells and the surrounding tissue. MSM is also important in the transport of electrolytes, signal compounds and subatomic particles. This soft connective tissue that it creates is the essential communications network within the body, in this case the scalp, through the transfer of bio information. MSM is also present in Keratin, the so-called tough protein substance in hair Biotin in Formula III is derived from the B vitamin family. Biotin helps produce keratin, the protein that builds hair. Studies have shown a deficiency in this water soluble vitamin can lead to hair loss. Biotin is also necessary for cell growth and has the formula:

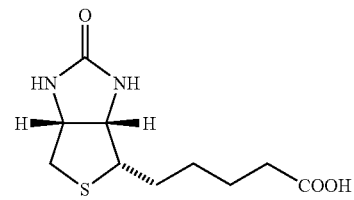 [SMILES: O=C(O)CCCC[C@@H]1SC[C@@H]2NC(=O)N[C@@H]21]

In Formula III, Green Tea Extract, called EGCG or Epigallocatechin Gallate, and associated with higher levels of sex hormone binding globulin (SBHG), is used to inhibit the 5-alpha reductase enzyme which converts testosterone to DHT, as mentioned earlier. Increased SBHG is believed to help to reduce the effects of androgenetic alopecia (baldness). SBHG binds with a high affinity to testosterone, which makes it not bioactive and cannot bind to androgen receptors or be converted into dihydrotestosterone (DHT). Another key molecule found in Green Tea is catechins. Studies have shown catechins to relax arteries, thus aiding in cardiovascular activity and microcapillary circulation to hair follicles. Antioxidants are another benefit to the use of Green Tea.

L-Lysine, an amino acid, is an essential ingredient to Formula IV. It has the formula:

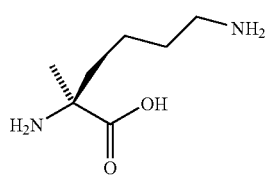

It promotes hair growth and research has shown that it accelerates the growth process. (See, for example http://www-.blackwell-synergy.com/doi/abs/10.1046/j.0412-5463.20 01.00110.x?journalCode=ics&volume=24&issue=1. Also hair loss is associated with suboptimal levels of L-lysine. By correcting the imbalance, hair loss stops and its health and vitality is returned.

Grape Seed Extract in Formula IV was observed to promote hair growth by over 200%. It is believed that Proanthyocyanidins in Grape Seed is a powerful stimulus. The seed oil also contains vitamins E, C as well as beta-carotene, which are antioxidants that neutralize free radicals that damage hair. This oil also acts as a carrier for other nutrients that are contained in Formula IV Additionally, L-Arginine in Formula IV is another amino acid that's involved with hair growth. It does this by producing a Nitric Oxide gas which dilates the blood vessels, thus increasing circulation and the transport of nutrients. This Nitric Oxide gas that is created by this amino acid is the one of the modes of activity that is found in the well known treatment of Minoxidil. The formula for L-Arginine is given by:

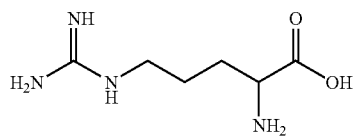 [SMILES: N=C(N)NCCCC(N)C(=O)O]

It will be understood that Formulae I, II, III and IV may be designed using the respective antiandrogen ingredients at various formulations. However, it has been found that desirable emulsification of the ingredients is possible with certain design features. These include the following compounding solutions in phases A, B and C as shown below:

| Chemical Name | Phase | % by weight | % range |
|---|---|---|---|
| Water | A | 84.11% | 83-85% |
| Lysine HCl | A | 0.81% | 0.7-0.9% |
| Arginine | A | 0.81% | 0.7-0.9% |
| Dimethyl Sulfone/MSM | A | 1.62% | 1.5-1.7% |
| Emu Oil | B | 4.72% | 3.5-5.0% |
| Steareth-20 | B | 3.25% | 3.0-3.5% |
| Steareth-2 | B | 1.62% | 1.5-1.7% |
| *Serenoa Serrulata** | C | 0.81% | 0.7-0.9% |

-continued

| Chemical Name | Phase | % by weight | % range |
|---|---|---|---|
| *Camellia Sineensis*** | C | 0.26% | 0.20-0.29% |
| *Ginkgo Biloba* Extract | C | 0.26% | 0.20-0.29% |
| *Vitis Vinifera**** | C | 0.26% | 0.20-0.29% |
| Biotin | C | 0.01% | 0.01-0.02% |
| Silica | C | 0.26% | 0.20-0.29% |
| Copper Tripeptide-1 | C | 0.26% | 0.20-0.29% |
| Fragrance | C | 0.51% | 0.49-0.53% |
| Phenagon PDI**** | C | 0.43% | 0.41-0.45% |
| TOTAL | | 100.00% | |

*Saw Palmetto Extract
**Green Tea Extract
***Grape Seed Extract
****Phenoxyethanol (and) DMDM Hydantoin (and) Iodopropynyl Butylcarbamate Emulsification of the ingredients was most effectively affected by: adding phase A ingredients to a main tank; mixing the ingredients at 1200 revolutions per minute (rpm) for 30 minutes while heating to 180° F.; and then sampling the resulting product to make sure that all the ingredients are completely dissolved; in a separate tank, mixing phase B ingredients and heating to 180° F. and then adding phase B ingredients to phase A mixture while agitating at 1800 rpm for 45 minutes; then starting to cool down the resulting mixture A & B and when temperature reaches 110° F., adding phase C ingredients, one at a time while mixing at 1200 rpm between additions.

Though these numerous details of the disclosed method are set forth here, such as process parameters, to provide an understanding of the present disclosure, it will be obvious, however, to those skilled in the art that these specific details need not be employed to practice the present embodiments. At the same time, it will be evident that the same methods may be employed in other similar process steps that are too many to cite, such as the order in which the phase ingredients are mixed and stirred at varying rates and temperatures. Also, further experimentation with some variations in these parameters may also promote growth of new hair. In addition, the disclosed hair sustaining formulation can be prepared to be administered as a solution, lotion, cream micelle, spray, gel or roller stick.

While the invention has been particularly shown and described with reference to a particular embodiment(s), it will be appreciated that variations of the above-disclosed embodiments(s) and other features and function, or alternatives thereof, may be desirably combined into many other different systems or applications Also that various presently unforeseen and unanticipated alternatives, modifications, variations or improvements therein may be subsequently made by those skilled in the art which are also intended to be encompassed by the following claims.

What is claimed is:

1. A topical hair sustaining formulation having a liquid transport agent and multi-ingredients, wherein the liquid transport agent carries said multi-ingredients to hair follicles in order to prevent Dihydrotestosterone (DHT) from attaching to receptor sites on the follicles of existing hair; wherein said liquid transport agent comprises emu oil compound in a range from about 3.5 to 3.5% by weight; wherein said multi-ingredients comprise water from about 83 to 85% by weight, Lysine HCI, Arginine, Dimethyl Sulfone, Steareth-20, Steareth-2, Camellia Sinensis, *Ginkgo Biloba* extract, *Vitis Vinifera*, Biotin, Silica, Copper Tripeptide-1, fragrance, a cosmetic preservative comprising phenoxyethanol, DMDM hydantoin and iodopropynyl butylcarbamate; and antiandrogen ingredients comprising *Serenoa Serrulata* (Saw Palmetto), Copper Peptide and Methylsulfonylmethane (MSM).

2. The hair sustaining formulation according to claim 1, wherein the concentration of Lysine HCl in said formulation ranges from about 0.7 to about 0.9% by weight.

3. The hair sustaining formulation according to claim 1, wherein the concentration of Arginine in said formulation ranges from about 0.7 to about 0.9% by weight.

4. The hair sustaining formulation according to claim 1, wherein the concentration of Dimethyl Sulfone in said formulation ranges from about 1.5 to about 1.7% by weight.

5. The hair sustaining formulation according to claim 1, wherein the concentration of Steareth-20 in said formulation ranges from about 3.0 to about 3.5% by weight.

6. The hair sustaining formulation according to claim 1, wherein the concentration of Steareth-2 in said formulation ranges from about 1.5 to about 1.7% by weight.

7. The hair sustaining formulation according to claim 1, wherein the concentration of Serenoa Serrulata in said formulation ranges from about 0.7 to about 0.9% by weight.

8. The hair sustaining formulation according to claim 1, wherein the concentration of Camellia Sinensis ranges from about 0.20 to about 0.29% by weight, and that of Ginkgo Biloba Extract ranges from about 0.20 to about 0.29% by weight in said formulation.

9. The hair sustaining formulation according to claim 1, wherein the concentration of Vitis Vinifera ranges from about 0.20 to about 0.29% by weight, and that of Biotin ranges from about 0.01 to about 0.02% by weight in said formulation.

10. The hair sustaining formulation according to claim 1, wherein the concentration of Silica ranges from about 0.20 to about 0.29% by weight, and that of Copper Tripeptide-1 ranges from about 0.20 to about 0.29% by weight in said formulation.

11. The hair sustaining formulation according to claim 1, wherein the concentration of Fragrance ranges from about 0.49 to about 0.53% by weight, and that of a cosmetic preservative comprising phenoxyethanol, DMDM hydantoin and iodopropynyl butylcarbamate ranges from about 0.41 to about 0.45% by weight in said formulation.

* * * * *